United States Patent
Gupta et al.

(10) Patent No.: US 11,624,937 B2
(45) Date of Patent: Apr. 11, 2023

(54) DEVICE TO PREVENT RETINAL HYPOXIA

(71) Applicant: ACUCELA INC., Seattle, WA (US)

(72) Inventors: Amitava Gupta, Roanoke, VA (US); Ryo Kubota, Seattle, WA (US)

(73) Assignee: ACUCELA INC., Seattle, WA (US)

(*) Notice: Subject to any disclaimer, the term of this patent is extended or adjusted under 35 U.S.C. 154(b) by 0 days.

(21) Appl. No.: 17/250,278

(22) PCT Filed: Jul. 3, 2019

(86) PCT No.: PCT/US2019/040580
§ 371 (c)(1),
(2) Date: Dec. 23, 2020

(87) PCT Pub. No.: WO2020/014074
PCT Pub. Date: Jan. 16, 2020

(65) Prior Publication Data
US 2021/0263336 A1    Aug. 26, 2021

Related U.S. Application Data

(60) Provisional application No. 62/694,971, filed on Jul. 7, 2018.

(51) Int. Cl.
*G02C 7/02* (2006.01)
*G02C 7/04* (2006.01)
(Continued)

(52) U.S. Cl.
CPC .............. *G02C 7/022* (2013.01); *G02C 7/021* (2013.01); *G02C 7/04* (2013.01); *G02C 7/049* (2013.01); *G02C 11/04* (2013.01); *G02C 11/10* (2013.01)

(58) Field of Classification Search
CPC ........ G02C 7/021; G02C 7/022; G02C 7/027; G02C 7/04; G02C 7/049; G02C 7/083; G02C 2202/10; G02C 11/04; G02C 11/10
See application file for complete search history.

(56) References Cited

U.S. PATENT DOCUMENTS

| 6,516,808 B2* | 2/2003 | Schulman ............ A61B 5/1473 128/899 |
| 7,018,040 B2 | 3/2006 | Blum |

(Continued)

FOREIGN PATENT DOCUMENTS

| EP | 3153139 | 4/2017 |
| EP | 3413116 | 12/2018 |

(Continued)

OTHER PUBLICATIONS

Adler, Daniel, et al., "The possible effect of under correction on myopic progression in children," Clin Exp Optom., 89:315-321 (2006).

(Continued)

*Primary Examiner* — Jordan M Schwartz
(74) *Attorney, Agent, or Firm* — Fisherbroyles LLP; John Shimmick (57) ABSTRACT

A contact lens configured to decrease dark adaptation comprises one or more LEDs and directs light from the LED away from the fovea and toward the parafovea or perifoveal regions of the retain. In some embodiments, soft contact lens embedded with one or more arrays of microLEDs and electronics operating the LEDs is configured to be worn at night in order to inhibit dark adaptation and reduce oxygen consumption by the rods. The contact lens may be made of a single layer of a contact lens material or multiple layers sandwiching a flexible transparent plastic layer comprising the electronics and the LED arrays. The contact lens may be made of a hydrophilic hydrogel material that is biocompatible to the human cornea, or a silicone hydrogel material. The contact lens may be spherical and may provide refractive correction to the eye of the wearer.

20 Claims, 6 Drawing Sheets

(51) Int. Cl.
*G02C 11/04* (2006.01)
*G02C 11/00* (2006.01)

(56) References Cited

U.S. PATENT DOCUMENTS

| | | |
|---|---|---|
| 8,246,167 B2 | 8/2012 | Legerton |
| 8,432,124 B2 | 4/2013 | Foster |
| 8,662,664 B2 | 3/2014 | Artal Soriano |
| 8,857,983 B2 | 10/2014 | Pugh |
| 9,345,813 B2 | 5/2016 | Hogg |
| 9,482,882 B1 | 11/2016 | Hanover |
| 9,482,883 B1 | 11/2016 | Meisenholder |
| 9,726,904 B1 | 8/2017 | Lin |
| 9,763,827 B2 | 9/2017 | Kelleher |
| 9,885,884 B2 | 2/2018 | Drobe |
| 9,918,894 B2 | 3/2018 | Lam |
| 9,962,071 B2 | 5/2018 | Yates |
| RE47,006 E | 8/2018 | To |
| 10,133,092 B2 | 11/2018 | Tsubota |
| 10,139,521 B2 | 11/2018 | Tran |
| 10,146,067 B2 | 12/2018 | Tsai |
| 10,231,897 B2 | 3/2019 | Tse |
| 10,268,050 B2 | 4/2019 | To |
| 10,288,909 B1* | 5/2019 | Youssef ............... H04B 1/48 |
| 10,591,745 B1 | 3/2020 | Lin |
| 10,788,686 B2 | 9/2020 | Tsai |
| 10,884,264 B2 | 1/2021 | Hones |
| 10,921,612 B2 | 2/2021 | Zhou |
| 10,993,515 B1 | 5/2021 | Kim |
| 11,000,186 B2 | 5/2021 | Linder |
| 11,163,166 B1 | 11/2021 | Ebert |
| 11,187,921 B2 | 11/2021 | Zhou |
| 11,219,287 B1 | 1/2022 | Kim |
| 11,281,022 B2 | 3/2022 | Buscemi |
| 11,320,674 B2 | 5/2022 | Kubota |
| 11,358,001 B2 | 6/2022 | Kubota |
| 11,366,339 B2 | 6/2022 | Kubota |
| 11,366,341 B1 | 6/2022 | Kubota |
| 11,402,662 B2 | 8/2022 | Wyss |
| 11,409,136 B1 | 8/2022 | Kubota |
| 2002/0186345 A1 | 12/2002 | Duppstadt |
| 2003/0011745 A1 | 1/2003 | Molebny |
| 2004/0237971 A1 | 12/2004 | Radhakrishnan |
| 2004/0246441 A1 | 12/2004 | Stark |
| 2004/0257529 A1 | 12/2004 | Thomas |
| 2005/0258053 A1 | 11/2005 | Sieg |
| 2006/0082729 A1 | 4/2006 | To |
| 2007/0002452 A1 | 1/2007 | Munro |
| 2007/0076217 A1 | 4/2007 | Baker |
| 2007/0115431 A1 | 5/2007 | Smith, III |
| 2007/0127349 A1 | 6/2007 | Hotta |
| 2008/0291391 A1 | 11/2008 | Meyers |
| 2008/0309882 A1 | 12/2008 | Thorn |
| 2009/0002631 A1 | 1/2009 | Campbell |
| 2009/0187242 A1 | 7/2009 | Weeber |
| 2009/0204207 A1 | 8/2009 | Blum |
| 2010/0076417 A1 | 3/2010 | Suckewer |
| 2010/0294675 A1 | 11/2010 | Mangano |
| 2010/0296058 A1 | 11/2010 | Ho |
| 2011/0085129 A1 | 4/2011 | Legerton |
| 2011/0153012 A1 | 6/2011 | Legerton |
| 2011/0157554 A1 | 6/2011 | Kawai |
| 2011/0202114 A1 | 8/2011 | Kessel |
| 2012/0055817 A1 | 3/2012 | Newman |
| 2012/0062836 A1 | 3/2012 | Tse |
| 2012/0199995 A1 | 8/2012 | Pugh |
| 2012/0206485 A1 | 8/2012 | Osterhout |
| 2012/0212399 A1 | 8/2012 | Border |
| 2012/0215291 A1 | 8/2012 | Pugh |
| 2013/0027655 A1 | 1/2013 | Blum |
| 2013/0194540 A1 | 8/2013 | Pugh |
| 2013/0278887 A1* | 10/2013 | Legerton ............... A61B 3/0008 351/158 |
| 2014/0039048 A1 | 2/2014 | Olof |
| 2014/0039361 A1 | 2/2014 | Siu |
| 2014/0194773 A1 | 7/2014 | Pletcher |
| 2014/0218647 A1 | 8/2014 | Blum |
| 2014/0240665 A1 | 8/2014 | Pugh |
| 2014/0268029 A1 | 9/2014 | Pugh |
| 2014/0277291 A1 | 9/2014 | Pugh |
| 2014/0379054 A1 | 12/2014 | Cooper |
| 2015/0057701 A1 | 2/2015 | Kelleher |
| 2015/0109574 A1 | 4/2015 | Tse |
| 2015/0160477 A1 | 6/2015 | Dai |
| 2015/0200554 A1 | 7/2015 | Marks |
| 2015/0241706 A1 | 8/2015 | Schowengerdt |
| 2016/0056498 A1 | 2/2016 | Flitsch |
| 2016/0067037 A1 | 3/2016 | Rosen |
| 2016/0067087 A1 | 3/2016 | Tedford |
| 2016/0091737 A1* | 3/2016 | Kim ..................... G02C 11/10 351/158 |
| 2016/0143801 A1 | 5/2016 | Lam |
| 2016/0158486 A1 | 6/2016 | Colbaugh |
| 2016/0212404 A1 | 7/2016 | Maiello |
| 2016/0270656 A1 | 9/2016 | Samec |
| 2016/0377884 A1 | 12/2016 | Lau |
| 2017/0000326 A1 | 1/2017 | Samec |
| 2017/0001032 A1 | 1/2017 | Samec |
| 2017/0010480 A1 | 1/2017 | Blum |
| 2017/0014074 A1 | 1/2017 | Etzkorn |
| 2017/0055823 A1 | 3/2017 | Lu |
| 2017/0072218 A1 | 3/2017 | Rucker |
| 2017/0078623 A1 | 3/2017 | Hilkes |
| 2017/0097519 A1* | 4/2017 | Lee ........... A61B 3/10 |
| 2017/0184875 A1* | 6/2017 | Newman ............... G02C 7/022 |
| 2017/0229730 A1* | 8/2017 | Flitsch .............. H01M 10/0568 |
| 2017/0236255 A1 | 8/2017 | Wetzstein |
| 2017/0270636 A1* | 9/2017 | Shtukater ............... G02C 11/10 |
| 2017/0276963 A1 | 9/2017 | Brennan |
| 2017/0307779 A1 | 10/2017 | Marullo |
| 2018/0017810 A1 | 1/2018 | Wu |
| 2018/0017814 A1* | 1/2018 | Tuan ..................... G02C 11/10 |
| 2018/0052319 A1 | 2/2018 | McCabe |
| 2018/0055351 A1* | 3/2018 | Yates ..................... A61B 3/135 |
| 2018/0074322 A1 | 3/2018 | Rousseau |
| 2018/0090958 A1 | 3/2018 | Steger |
| 2018/0092738 A1* | 4/2018 | Tai ............................. A61F 2/16 |
| 2018/0136486 A1 | 5/2018 | Macnamara |
| 2018/0136491 A1 | 5/2018 | Ashwood |
| 2018/0161231 A1 | 6/2018 | Tse |
| 2018/0173010 A1 | 6/2018 | Harant |
| 2018/0188556 A1 | 7/2018 | Portney |
| 2018/0221140 A1 | 8/2018 | Rosen |
| 2018/0264284 A1 | 9/2018 | Alvarez |
| 2018/0275427 A1 | 9/2018 | Lau |
| 2018/0345034 A1 | 12/2018 | Butzloff |
| 2019/0033618 A1 | 1/2019 | Choi |
| 2019/0033619 A1 | 1/2019 | Neitz |
| 2019/0038123 A1 | 2/2019 | Linder |
| 2019/0049730 A1 | 2/2019 | Miller |
| 2019/0076241 A1 | 3/2019 | Alarcon Heredia |
| 2019/0092545 A1 | 3/2019 | Oag |
| 2019/0107734 A1* | 4/2019 | Lee ........................ A61F 2/1624 |
| 2019/0113757 A1* | 4/2019 | Van Heugten ..... G02B 27/0172 |
| 2019/0129204 A1 | 5/2019 | Tsubota |
| 2019/0227342 A1 | 7/2019 | Brennan |
| 2019/0235279 A1 | 8/2019 | Hones |
| 2019/0247675 A1 | 8/2019 | Legerton |
| 2019/0250432 A1 | 8/2019 | Kim |
| 2019/0314147 A1 | 10/2019 | Blum |
| 2020/0033637 A1 | 1/2020 | Jamshidi |
| 2020/0089023 A1 | 3/2020 | Zhou |
| 2020/0110265 A1 | 4/2020 | Serdarevic |
| 2020/0133024 A1 | 4/2020 | Paune Fabre |
| 2020/0142219 A1 | 5/2020 | Rousseau |
| 2020/0183169 A1 | 6/2020 | Peng |
| 2020/0360184 A1* | 11/2020 | Xiao ....................... A61F 9/009 |
| 2021/0018762 A1 | 1/2021 | Zheleznyak |
| 2021/0031051 A1 | 2/2021 | Kubota |
| 2021/0048690 A1 | 2/2021 | Guillot |
| 2021/0069524 A1 | 3/2021 | Kubota |
| 2021/0231977 A1 | 7/2021 | Zhou |
| 2021/0298440 A1 | 9/2021 | Kim |
| 2021/0329764 A1 | 10/2021 | Linder |

(56) References Cited

U.S. PATENT DOCUMENTS

| | | |
|---|---|---|
| 2021/0356767 A1 | 11/2021 | Kubota |
| 2021/0379399 A1 | 12/2021 | Buscemi |
| 2021/0382325 A1 | 12/2021 | Kubota |
| 2021/0382326 A1 | 12/2021 | Kubota |
| 2021/0389607 A1 | 12/2021 | Buscemi |

FOREIGN PATENT DOCUMENTS

| | | |
|---|---|---|
| KR | 20180038359 | 4/2018 |
| KR | 20180038359 A | 4/2018 |
| TW | 201234072 | 8/2012 |
| WO | 2009074638 A2 | 6/2009 |
| WO | 2009121810 A1 | 10/2009 |
| WO | 2010015255 A1 | 2/2010 |
| WO | 2010043599 A1 | 4/2010 |
| WO | 2011089042 A1 | 7/2011 |
| WO | 2012136470 A1 | 10/2012 |
| WO | 2013087518 A1 | 6/2013 |
| WO | 2013158418 | 10/2013 |
| WO | 2014033035 A1 | 3/2014 |
| WO | 2014191460 A1 | 12/2014 |
| WO | 2015063097 A1 | 5/2015 |
| WO | 2015186723 | 12/2015 |
| WO | 2015192117 | 12/2015 |
| WO | 2017094886 | 6/2017 |
| WO | 2017097708 | 6/2017 |
| WO | 2018014712 | 1/2018 |
| WO | 2018014960 | 1/2018 |
| WO | 2018085576 | 5/2018 |
| WO | 2018088980 | 5/2018 |
| WO | 2018208724 | 11/2018 |
| WO | 2019114463 | 6/2019 |
| WO | 2019191510 | 10/2019 |
| WO | 2019217241 | 11/2019 |
| WO | 2020014074 | 1/2020 |
| WO | 2020014613 | 1/2020 |
| WO | 2020028177 | 2/2020 |
| WO | 2020069232 | 4/2020 |
| WO | 2021022193 | 2/2021 |
| WO | 2021056018 | 3/2021 |
| WO | 2021168481 | 8/2021 |
| WO | 2021231684 | 11/2021 |
| WO | 2021252318 | 12/2021 |
| WO | 2021252319 | 12/2021 |
| WO | 2021252320 | 12/2021 |

OTHER PUBLICATIONS

Aleman, Andrea C., et al.,, "Reading and Myopia: Contrast Polarity Matters," Scientific Reports, 8 pages (2018).

Arden, G.B., et al., "Does dark adaptation exacerbate diabetic retinopathy? Evidence and a linking hypothesis," Vision Research 38:1723-1729 (1998).

Arden, GB, et al., "Regression of early diabetic macular edema is associated with prevention of dark adaptation", in Eye, (2011). 25, pp. 1546-1554.

Benavente-Perez, A., et al., "Axial Eye Growth and Refractive Error Development Can BE Modified by Exposing the Peripheral Retina to Relative Myopic or Hyperopic Defocus," Invest Ophthalmol Vis Sci., 55:6765-6773 (2014).

Bonar, Jr, et al., "High brightness low power consumption microLED arrays", in SPIE DigitalLibrary.org/conference-proceedings-of-spie, SPIE OPTO, 2016, San Francisco, California, United States, Abstract Only.

Carr, Brittany J., et al., "The Science Behind Myopia," retrieved from https://webvision.med.utah.edu/book/part-xvii-refractive-errors/the-science-behind-myopia-by-brittany-j-carr-and-william-k-stell/, 89 pages (2018).

Chakraborty, R., et al., "Diurnal Variations in Axial Length, Choroidal Thickness, Intraocular Pressure, and Ocular Biometrics," IOVS, 52(8):5121-5129 (2011).

Chakraborty, R., et al., "Hyperopic Defocus and Diurnal Changes in Human Choroid and Axial Length," Optometry and Visual Science, 90(11):1187-1198 (2013).

Chakraborty, R., et al., "Monocular Myopic Defocus and Daily Changes in Axial Length and Choroidal Thickness of human Eyes," Exp Eye Res, 103:47-54 (2012).

Cooper, J., et al., "Current status of the development and treatment of myopia", Optometry, 83:179-199 (2012).

Cooper, J., et al., "A Review of Current Concepts of the Etiology and Treatment of Myopia," Eye & Contact Lens, 44(4):231-247 (Jul. 2018).

Demory, B., et al., "Integrated parabolic microlenses on micro LED color pixels", in Nanotechnology, (2018); 29, 16, pp. 1018, Abstract Only.

Dolgin, Elie, "The Myopia Boom," Nature 519:276-278 (2015).

Edrington, Timothy B., "A literature review: The impact of rotational stabilization methods on toric soft contact lens performance," Contact Lens & Anterior Eye, 34:104-110 (2011).

Flitcroft, D.I., "The complex interactions of retinal, optical and environmental factors in myopia aetiology," 31(6):622-660 (2012).

Garner, L.F., et al., "Crystalline Lens Power in Myopia," Optometry and Vision Science, 69:863-865 (1992).

Gwiazda, Jane, "Treatment Options for Myopia," retrieved from https://www.ncbi.nlm.nih.gov/pmc/articles/PMC2729053/, Optom Vis Sci., 86(6):624-628 (Jun. 2009).

Gwiazda, Jane, et al., "A Randomized Clinical Trial of Progressive Addition Lenses versus Single Vision Lenses on the Progression of Myopia in Children", Invest Ophthalmol Vis Sci, 44:1492-500 [PubMed: 12657584] (2003).

Hammond, D.S., et al., "Dynamics of active emmetropisation in young chicks—influence of sign and magnitude of imposed defocus" Ophthalmic Physiol Opt. 33:215-222 (2013).

Henry W., "MicroLED Sources enable diverse ultra-low power applications", in Photonic Spectra, 2013.

International Search Report and Written Opinion for International Application No. PCT/US2019/040580, 13 pages (dated Sep. 26, 2019).

Jones, D., "Measure Axial Length to Guide Myopia Management," Review of Myopia Management, 5 pages (Apr. 9, 2020).

Kur, Joanna, et al., "Light adaptation does not prevent early retinal abnormalities in diabetic rats," Scientific Reports, 8 pages (Feb. 8, 2016).

Lagreze, Wolf A., et al., "Preventing Myopia," retrieved from https://www.ncbi.nlm.nih.gov/pmc/articles/PMC5615392/, Dtsch Arztebl Int., 114(35-36):575-580 (Sep. 2017).

Lam, Carly Siu Yin, et al., "Defocus Incorporated Multiple Segments (DIMS) spectacle lenses slow myopia progression: a 2-year randomised clinical trial," Br. J. Ophthalmol. 0:1-6 (2019).

Leo, Seo-Wei, et al., "An evidence-based update on myopia and interventions to retard its progression," J AAPOS, 15(2):181-189 (Apr. 2011).

Lingley, A.R., et al., : A single pixel wireless contact lens display, in J Micromech. Microeng., 2011; 21, 125014; doi:10.1088/0960-1317/21/12/125014, Abstract Only.

Martin, J.A., et al., "Predicting and Assessing Visual Performance with Multizone Bifocal Contact Lenses," Optom Vis Sci, 80(12):812-819 (2003).

Matkovic, K., et al., "Global Contrast Factor—a New Approach to Image Contrast," Computational Aesthetics in Graphics, Visualization and Imaging, 9 pages (2005).

McKeague C, et al. "Low-level night-time light therapy for age-related macular degeneration (ALight): study protocol for a randomized controlled trial", in Trials 2014, 15:246, http://www.trialsjournal.com/content/15/1/246.

Moreno, I, "Creating a desired lighting pattern with an LED array" in Aug. 2008, Proceedings of SPIE—The International Society for Optical Engineering 7058, DOI: 10.1117/12.795673.

Moreno, I., "Modeling the radiation pattern of LEDS", in Optics Express, 2008; 16, 3 pp. 1808.

Nickla, Debora L., et al., "Brief hyperopic defocus or form deprivation have varying effects on eye growth and ocular rhythms depending on the time-of-day of exposure," Exp Eye Res. 161:132-142 (Aug. 2017).

(56) References Cited

OTHER PUBLICATIONS

Ramsey, DJ, and Arden, GB, "Hypoxia and dark adaptation in diabetic retinopathy: Interactions, consequences and therapy", in Microvascular Complications—Retinopathy (JK Sun, ed.), Cur Dab Rep (2015) 15: 118, DOI 10.1007/s11892-015-0686-2, Abstract Only.

Read, Scott A., et al., "Choroidal changes in human myopia: insights from optical coherence tomography imaging," Clin Exp Optom, 16 pages (2018).

Read, Scott A., et al., "Human Optical Axial Length and Defocus," IOVS, 51(12):6262-6269 (2010).

Shivaprasad, S, et al., "Clinical efficacy and safety of a light mask for prevention of dark adaptation in treating and preventing progression of early diabetic macular oedema at 24 months (CLEOPATRA): a multicentre, phase 3, randomised controlled trial," in www.thelancet.com/diabetes-endocrinology vol. 6, pp. 382-391 ( May 2018).

Smith, III, Earl L., "Optical treatment strategies to slow myopia progression: Effects of the visual extent of the optical treatment zone," retrieved from https://www.ncbi.nlm.nih.gov/pmc/articles/PMC3624048/, Exp Eye Res., 114:77-88 (Sep. 2013).

Srinivasan, S., "Ocular axes and angles: Time for better understanding," J. Cataract Refract. Surg., 42:351-352 (Mar. 2016).

Torii, Hidemasa, et al., "Violet Light Exposure Can Be a Preventive Strategy Against Myopia Progression," EBioMedicine 15:210-219 (2017).

Wallman, Josh, et al., "Homeostasis of Eye Growth and the Question of Myopia," Neuron, 43:447-468 (2004).

Wolffsohn, James A., et al., "Impact of Soft Contact Lens Edge Design and Midperipheral Lens Shape on the Epithelium and Its Indentation With Lens Mobility," IOVS, 54(9):6190-6196 (2013).

Haglund, Erik, et al., "Multi-wavelength VCSEL arrays using high-contrast gratings," Proc. of SPIE vol. 10113, 7 pages (2017).

International Application No. PCT/US2021/036100, filed Jun. 7, 2021 (86 pages).

International Patent Application No. PCT/US2021/032162, filed May 13, 2021 (58 pages).

International Patent Application No. PCT/US2021/036102, filed Jun. 7, 2021 (67 pages).

International Patent Application No. PCT/US2021/070166, filed Feb. 19, 2021 (79 pages).

Jayaraman, V., et al., "Recent Advances in MEMS-VCSELs for High Performance Structural and Functional SS-OCT Imaging," Proc. of SPIE vol. 8934, retrieved from http://proceedings.spiedigitallibrary.org/ on Dec. 1, 2015 (2014).

U.S. Appl. No. 17/304,666, filed Jun. 24, 2021 (67 pages).
U.S. Appl. No. 17/302,479, filed May 4, 2021 (60 pages).
U.S. Appl. No. 17/302,827, filed May 13, 2021 (52 pages).
U.S. Appl. No. 17/303,889, filed Jun. 9, 2021 (69 pages).
U.S. Appl. No. 17/304,630, filed Jun. 23, 2021 (68 pages).
U.S. Appl. No. 17/304,691, filed Jun. 24, 2021 (88 pages).

Cook, Colin A., et al., "Phototherapeutic Contact Lens for Diabetic Retinopahty," 2018 IEEE Micro Electro Mechanical Systems, pp. 62-65, XP033335512, (Jan. 21, 2018).

\* cited by examiner

DEVICE TO PREVENT RETINAL HYPOXIA

RELATED APPLICATIONS

This application is a 371 national phase of PCT/US2019/040580, filed Jul. 3, 2019, published as WO 2020/014074 on Jan. 16, 2020, which claims the benefit under 35 U.S.C. § 119(e) of filing date of U.S. Provisional Patent Application No. 62/694,971, filed Jul. 7, 2018 the disclosures of which are incorporated, in their entirety, by this reference.

BACKGROUND

Diabetic retinopathy (DR) can be a complication of type 1 and type 2 diabetes. Diabetic retinopathy can also be a lead to visual impairment and ultimately blindness. There is currently an epidemic of type 2 diabetes, and DR may become a more serious health problem in the future. The retina has three kinds of photoreceptors, rods, cones and intrinsically photosensitive retinal ganglion cells (IPRGC). The rods are more numerous than cones. For example, the eye can have 120,000,000 rods and 6,000,000 cones. Rods have a higher metabolic rate than cones. This higher metabolic rate allows rods to signal the absorption of single photon. This higher metabolic activity results in a greater blood supply going to rods. Although the rods are avascular, these cells are supplied by the choroidal capillary network. The amount of oxygen used by rods increases with dark adaptation. In darkness, the low oxygen effects other areas of the retina, because the rods act as 'sink' for oxygen supplied by the retinal circulation. With light adaptation, the amount of oxygen used by the rods decrease significantly. Prior analysis has shown that the amount of oxygen consumed by the photoreceptors is approximately halved in light.

It has been proposed that the high metabolic demand of photoreceptors in the dark will exacerbate retinal hypoxia and may be a primary cause of DR. It has also been proposed that preventing the rod photoreceptors from dark adapting may significantly reduce their metabolic demand, may lessen hypoxia and slow progression of DR. Preliminary trials on diabetic patients suggests that light exposure during the night to prevent the rods from dark adapting results in the improvement of visual function and regression of macular edema in diabetic patients.

Prior art devices that seek to provide illumination to the retina to prevent dark adaptation and reduce retinal hypoxia have been reported. These include light masks and contact lenses embedded with sealed microtubules filled with Tritium oxide that emits beta particles. These radioactive contact lenses have been referred to as "A glowing contact lens". The beta particles are absorbed by a phosphorescent coating on the inner surface of the tubules, emitting visible radiation, a development reported by researchers at Caltech. Light masks have been commercialized, for example, by Polyphotonix Medical. The light masks incorporate LED light sources emitting in the blue to green region of the spectrum. They are designed to be worn from 8 PM to 8 AM and to be recharged every day. These masks are reported to have a usable life of about 80 days.

The luminescent contact lens described by Caltech utilizes a radioisotope of hydrogen to generate the energy that stimulates the phosphor coating to emit radiation. Inclusion of such a device in a contact lens designed to be worn on the cornea on a regular basis for several hours per day may impose risks to the wearer and is not likely to be acceptable to the patients or caregivers. For example, contact lenses are expected to withstand rough handling during insertion and removal and cleaning. It is conceivable that the embedded tubules may fracture during such handling and release radioactive chemicals such as tritium oxide into the contact lens that could then be absorbed by the cornea. It is also possible that the intensity of illumination generated may be insufficient to provide an adequate level of retinal illumination.

The sleep mask marketed by Polyphotonics generates green and blue light is transmitted through the eyelids and the pupil and/or the sclera and the choroid. The device may generate 75 photopic cd/m² of light. Although this sleep mask may decrease dark adaptation, some aspects of this approach are less than ideal. One reported limitation of the light mask is that it may have a low compliance rate in at least some instances. Another limitation is that since about 99% of the emitted light may be blocked by the eyelids and possibly more blocked by the material of the mask itself, the magnitude of electrical energy to operate the mask is greater than ideal, which may result in battery recharging and at least some temperature elevation in at least some instances.

Another prior art device has a plastic cup made of a transparent silicone rubber contained light-emitting diodes. A concave surface is fitted on the closed lid of either a left or right eye. This device emits light. Similar to a light mask, this device may have less than ideal compliance in at least some instances.

One approach to measuring light associated with dark adaption is to quantify light in Trolands. The Troland is a measure of retinal illuminance, defined as follows:

$$T = L \times p$$

Where L is the photopic luminance in cd m$^{-2}$ and p is pupil area in mm$^2$.

A scotopic Troland is defined as:

$$T = L' \times p$$

Where L' is the scotopic luminance in cd m$^{-2}$ and p is pupil area in mm$^2$.

In light of the above, there is a need for safe and effective devices that will provide retinal illumination in the dark that will prevent dark adaptation and reduce oxygen demand.

SUMMARY

In some embodiments, a contact lens configured to decrease dark adaptation comprises one or more light sources and directs light from the one or more light sources away from the fovea and toward the parafovea or perifoveal regions of the retina. In some embodiments, a soft contact lens has embedded therein one or more arrays of microLEDs and electronics operating the LEDs, and the contact lens is configured to be worn at night in order to decrease dark adaptation and reduce oxygen consumption by the rods. In some embodiments, images from the LEDs are imaged within the eye, and the LEDs can be imaged in many ways such as on an image shell of the retina, in front of it, or behind it. The contact lens may be made of a single layer of a contact lens material or multiple layers sandwiching a flexible transparent plastic layer comprising the electronics and the LED arrays. The contact lens may be made of a hydrophilic hydrogel material that is biocompatible to the human cornea, or a silicone hydrogel material. The contact lens may be spherical and may provide refractive correction to the eye of the wearer. The contact lens may be provided with a base curve geometry that is designed to stabilize the lens on the eye against translation or rotation. The contact lenses can be either disposable or of planned replacement modality. The LED arrays can be designed to provide an optimum range of illumination intensities within a desired wavelength band. The LEDs may be triggered by an onboard sensor that may be actuated manually or automatically. The LED arrays may be powered by an onboard battery which might be a primary battery or be rechargeable.

DETAILED DESCRIPTION

The presently disclosed methods and apparatus are well suited for treating retinal disease by directing light away from a fovea of the eye to decrease dark adaptation. Although specific reference is made to light sources on a contact lens, the methods and apparatus disclosed herein with reference to a contact lens can be similarly configured to direct light to a location of the retina away from the fovea to decrease dark adaptation of the rods of the eye. A support comprising one or more of a contact lens, goggles or eyeglass frames can be coupled to a light source and configured to direct light to the retina of the eye away from the fovea as described herein. Although embodiments are disclosed with a support comprising a contact lens, in some embodiments the support comprises an eyeglass frames or goggles, in which the light source and associated optical components as described herein with reference to a contact lens are configured to direct light to the retina away from the fovea when the eyeglass frame or goggles have been placed on the wearer.

The methods and apparatus disclosed herein are well suited for combination with prior approaches to combining microelectronics and LEDs with contact lenses. For example, MicroLEDs have been embedded in soft contact lenses previously for display purposes, in particular for augmented or virtual reality applications, and some aspects of these prior approaches are suitable for incorporation in accordance with the presently disclosed embodiments.

MicroLEDs

Figure 1:
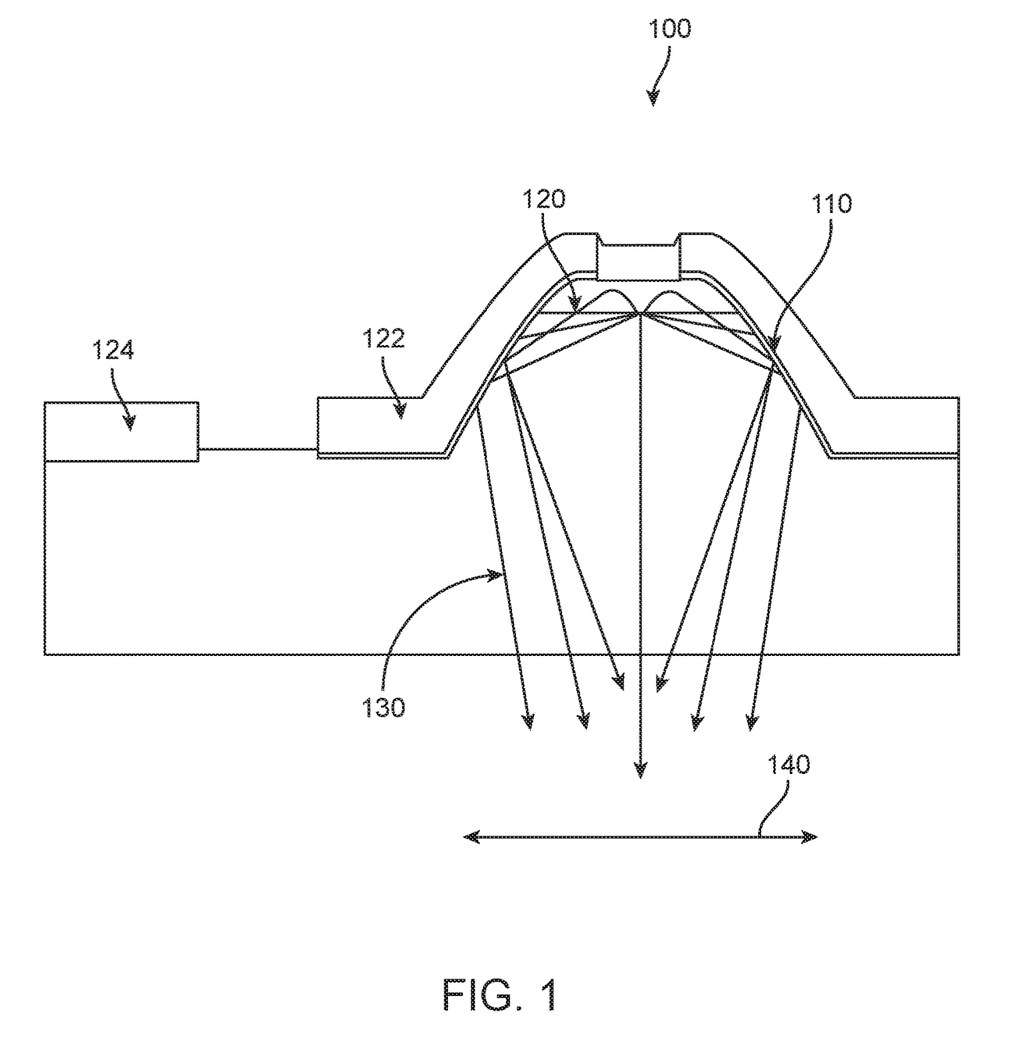
FIG. 1 shows the structure of a microLED, in accordance with some embodiments.

The microstructure of one or more LEDs 100, such as one or more microLED is shown in FIG. 1, demonstrating a design that collimates the light emitted by a microLED towards the front of the microLED, although other microLEDs can be used in accordance with the embodiments disclosed herein. In some embodiments, the microLED comprises a sidewall 110, which may provide total internal reflection of light 130. The light 130 is generated in a light emitting layer 120. The LED comprises an n contact 124 and a p contact 122. The light 130 is directed toward an area 140. The light beam near the one or more microLEDs 100 may comprise a cross-section of about 5 to 25 microns, and the light emitting area of the microLED and reflector may comprise similar dimensions. In some embodiments, the dimensions of the LED approximate a point source of light. In some embodiments, light from the LED is directed toward the eye in a substantially collimated configuration, for example with a diverging cone of light with an angle of no more than ten degrees, for example.

MicroLEDs can generate light with a drive current of about 5 nA, although other amounts of current can be used. In some embodiments, the individual structures are sufficiently small not to cause shadowing or loss of visual acuity through the lens, and may be located outside of an optical zone of a contact lens as described herein. MicroLEDs may be as small as 2 microns in diameter individually. They can maintain their quantum efficiency of emission, that is the efficiency of conversion of the electrical energy supplied to them to light, up to very high levels of energy input and can reach 8-10 million $cd/m^2$ of light output before losing quantum efficiency of light generation. Therefore a 10×10 microLED array each 2-4 microns and a pitch of 10 microns occupying an area of 0.15 mm×0.15 mm can generate up to 0.08-0.10 cd, or an illumination level of $4-5 \times 10^6$ $cd/m^2$ while a single microLED can generate about $8 \times 10^{-4}$ candelas, most of which can be delivered to the pupil, providing an illumination level of $7 \times 10^{-1}$ $cd/m^2$ over the pupillary aperture. This level of illumination is ample to overcome dark adaptation. Dark adaptation of the cones generally takes less than about 10 minutes. Dark adaptation of the rods generally takes less than 30 minutes, with substantial amounts of dark adaptation occurring from 10 to 20 minutes. An example of a dark adaptation curve is described in Pirenne, M H, "Dark adaptation and night vision", chapter 5 in Daysion, H, ed, The Eye, vol 2; London, Academic Press, 1962. About 10 nA of current driving a single microLED is sufficient to overcome dark adaptation. A preferred embodiment delivers illumination in the range of 0.05 to 5.0 cd over a 4 mm diameter pupil. Scotopic pupil sizes can vary from 2.5 mm to 8.00 mm in wearers in the age range 40 years or older.

In general, an upper level of light emitted (total over the whole contact lens eye contacting surface area may be no more than about 25 $cd/m^2$ for an extended time, e.g. 8 hours, when the wearer sleeps or is in the dark. An upper limit on the level of illumination over the pupil diameter (assumed to be 4 mm) can be 50 Photopic Trolands, and may be 10 scotopic trolands, peaked at 500 nm (+/−10 nm), for example. The peak of emission of a light emitting diode ("LED") of the contact lens as described herein can be within a range from about 490 nm to about 510 nm, for example. The therapeutic light can be delivered for an extended period of time, and the lens can be configured for extended substantially continuous wear, e.g. a week or more and user activated to provide therapeutic illumination as described herein, for example.

The contact lens as described herein can be configured to illuminate the rods of the eye in accordance with the distribution of rods and cones in the eye. The distribution of rods and cones in the eye can be determined with reference to the angle from the fovea, as is known to one of ordinary skill in the art. The density of rods is approximately 0 at the fovea and increases outward from the fovea. The density of cones at the fovea is approximately 140,000 receptors per $mm^2$. The density of cones about 10 degrees from the fovea is approximately 10,000. The density of rods at 10 degrees from the fovea is approximately 120,000 to 140,000 receptors per $mm^2$. A blind spot is located at approximately 15 to 20 degrees from the fovea. At approximately 20 degrees the density of rods is highest at about 150,000 to 160,000 receptors per mm². At greater distances from the fovea, the density of rods decreases from the peak value. For example, at 40 degrees from the fovea, the density is about 110,000 to 135,000 receptors per mm². An example of the density of rods and cones is provided on the worldwide web at the Wikipedia website (en.wikipedia.org/wiki/Photoreceptor_cell).

In some embodiments, a series of microLED arrays placed at the zone of the contact lens, corresponding to the peripheral zone of the retina that are rich in rods but lacking in cone density. The zone of the contact lens where the microLEDs are located may comprise an outer zone, such as an outer peripheral zone of the contact lens. The distribution of cones and rods in the retina, as described herein, enable the product design to place LED arrays away from the center of the contact lens, thus providing substantial oxygen permeability and high level of transparency at the optic zone. The optical zone of the contact lens can be configured to correct refractive error of the eye, for example to correct spherical and cylindrical refractive error of the eye.

Figure 2:
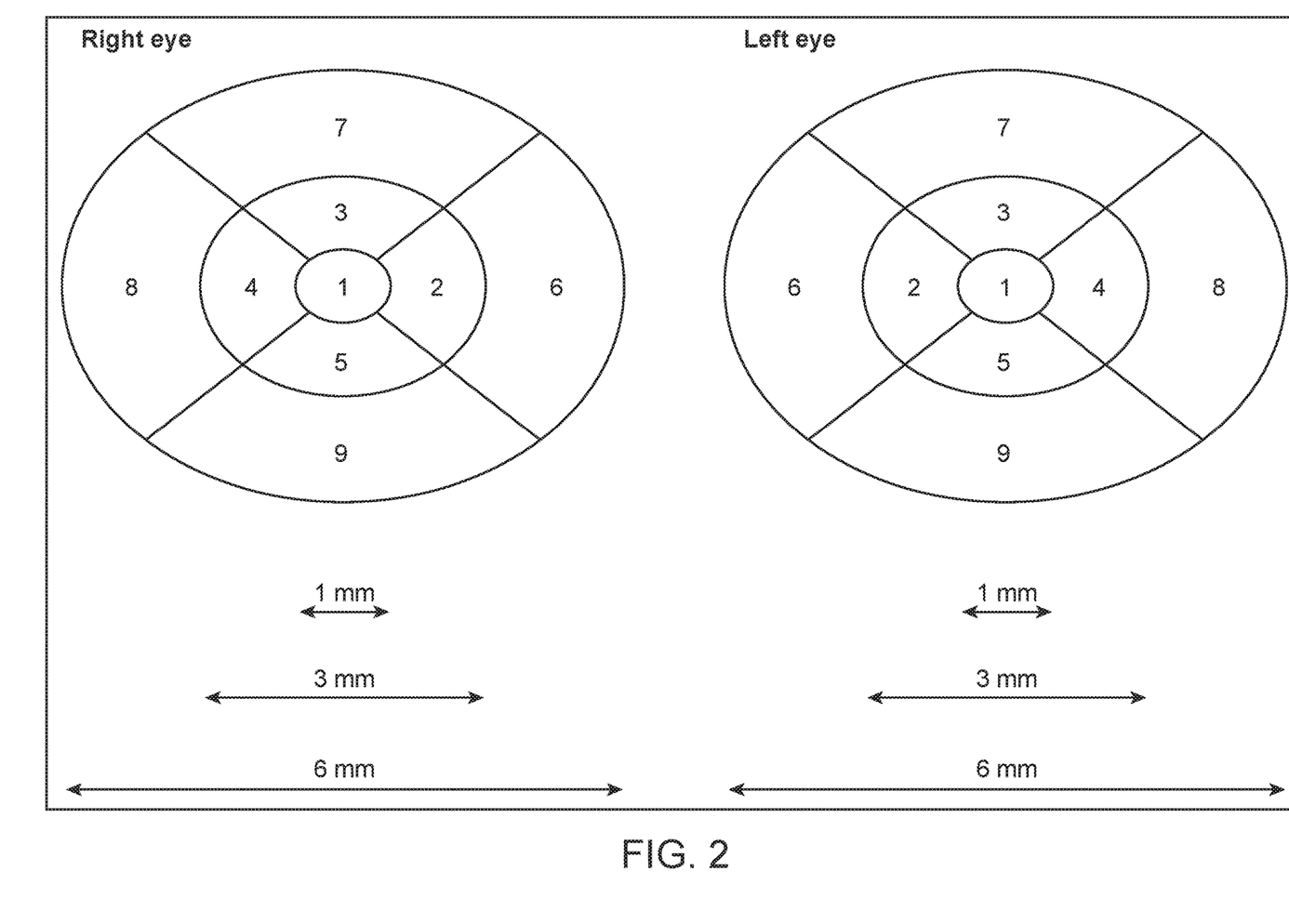
FIG. 2 shows sectors of the retina with different cone and rod densities, in accordance with some embodiments.

FIG. 2 shows sectors of the retina with different cone and rod densities. Sector 1 is the central foveolar (~500 microns In diameter), sectors 2-5 are parafoveal zones (diameter 2.5-3.0 mm, while sectors 6-9 are perifoveal zones (6 mm in diameter), in accordance with some embodiments. The contact lens as described herein can be configured to direct light to one or more of the parafoveal zones or the perifoveal zones of the retina. In some embodiments, the location of microLED arrays are located in the peripheral region of the lens, so that illumination from each array is incident on each of the subsectors of the retina, as shown in FIG. 2. Each of these microLED arrays may be 2×2, or 4×4 or 10×10 in size, wherein each LED may be 2 microns, 4 microns, 5 microns or 10 microns in diameter, and the array may have a pitch of 10 microns, 20 microns or 100 microns.

Figure 3A:
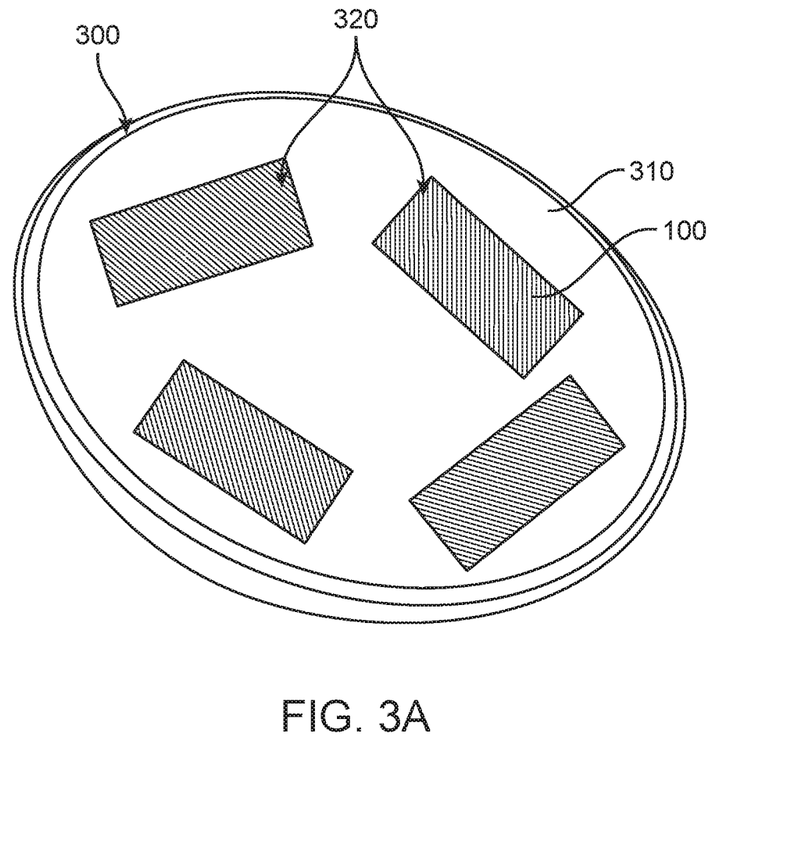
FIG. 3A shows a contact lens with embedded microLED arrays designed to illuminate parafoveal and perifoveal zones, in accordance with some embodiments.

FIG. 3A shows a contact lens 300 comprising a microLED array 320 embedded in a body 310 of a contact lens. The body 310 of the contact lens 300 may comprise a hydrogel material, such as a silicone hydrogel material. Each array 320 may comprise a plurality of LEDs 100. The arrays are preferably arranged along the periphery in quadrants, as shown in FIG. 3A. In some embodiments, a single microLED is located in each of the peripheral locations identified in FIG. 3A. In some embodiments, the contact lens comprises a single microLED disposed of anywhere within the contact lens. The single microLED can be configured to direct light to one or more of a parafoveal zone or a perifoveal zone as described herein.

In some embodiments, the wavelength of the emission by the microLEDs will match the peak light absorption of rods in the human retina, preferably in the range of 500 nm +/−10 nm. In some embodiments, bandwidth of the emitted radiation does not exceed +/−25 nm, because activation of cones can be possible, as the absorption coefficient of the rods decreases. The absorption spectra of the three types of cones and rods in the eye are known to one of ordinary skill in the art. For example, the blue cones, the green cones and the red cones have absorption peaks around 420 nm, 534 nm, and 564 nm, respectively. The rods have an absorption peak around 498 nm. The absorption coefficient of rods is 2-3 orders of magnitude higher than that of cones and retinal ganglion cells, so that the light intensity to be used to stimulate the rods and prevent dark adaptation can be much too low to stimulate the cones or the intrinsically photosensitive retinal ganglion cells ("IpRGC").

In some embodiments, a lens array such as a nanolens array is coupled to the microLED array in order to reduce the far field divergence. Light from a microLED can be largely Lambertian, but is best modeled as a Gaussian function with one or more sine and cosine functions in order to take into account reflections and waveguide effects. For a blue wavelength LED, the total emission can be 95% collimated within a 0.5 numerical aperture zone, a 3.5× improvement over the same LED without a lens structure. This corresponds to a half-width at half-maximum (HWHM) line width reduction of 2.85 times. Each lens in the nanolens array is preferably matched in terms of width and pitch to the microLEDs. The nanolens array may be spherical, aspherical, or aspheric lenses with prisms. Nano lenses may be passive or switchable.

Figure 3B:
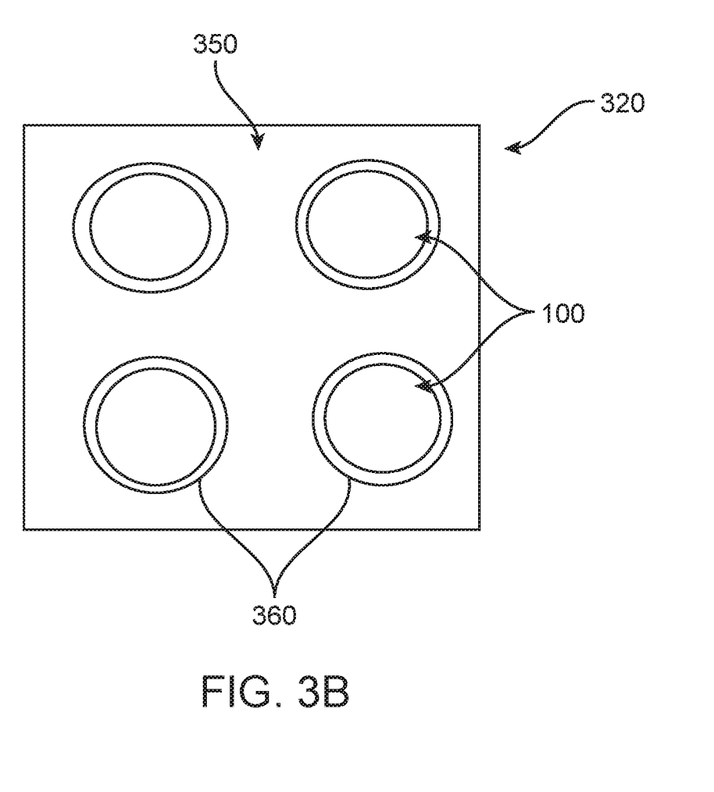
FIG. 3B shows an LED array and a lens array, in accordance with some embodiments.

FIG. 3B shows a plurality of lenses 360 placed in front of a plurality of LEDs 100 to direct light to the retina with a distribution of light as described herein. In some embodiments, the plurality of lenses is arranged in an array 350 and the plurality of LEDs is arranged in an array 320 with a similar pitch. The array of lenses 360 can be placed in front of LED array 350 to provide a desired light distribution on the retina as described herein. The array of lenses can be spaced apart from the LEDs of the LED array to provide an appropriate concentration of light on the retina, for example away from the fovea as described herein. The LED can be coupled to a reflector as described herein, in order to direct reflected light from the LED toward the lens with reflection from a curved surface, for example. In some embodiments, the plurality of lenses is spaced apart from the plurality of LEDs so as form an image of the LED near the retina, and the image of the LED can be formed on the retinal shell, before the retinal shell, or behind the retinal shell.

Electronics to Drive the microLEDs

Figure 4A:
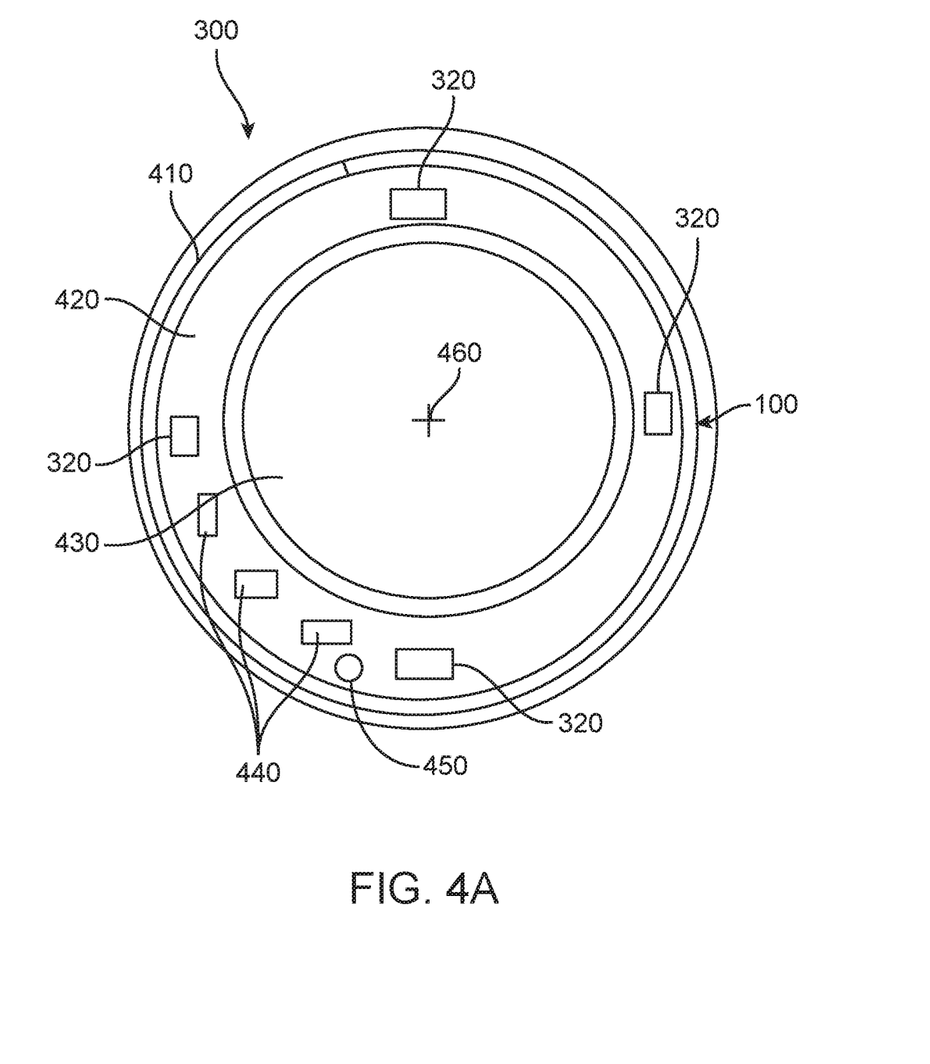
FIG. 4A shows a contact lens comprising a plurality of LEDS and circuitry to illuminate parafoveal and perifoveal zones, in accordance with some embodiments.

FIG. 4A shows a contact lens 300 with a plurality of LEDs 100 and electronics 440 comprising circuitry to illuminate parafoveal and perifoveal zones. The contact lens 300 may comprise an optical zone 430 to correct refractive error of the eye, electronics 440, microLED array 320, a sensor 450, and a printed circuit board 420 as described herein. The optical zone 430 may correct spherical and cylindrical refractive errors of the eye, and may comprise an optical axis 460 located near a center of the lens 300. In some embodiments, the contact lens 300 comprises an antenna 410. The electronics 440 can be mounted on a printed circuit board 420, such as a flexible printed circuit board comprising a modulus as described herein. The printed circuit 420 board may comprise a generally annular shape with the electronics mounted thereon. In some embodiments, the contact lens 300 comprises an antenna coupled to the electronics with a trace. The antenna can be mounted on the printed circuit board or may comprise a separate component embedded in the contact lens Although four microLED arrays are shown, in some embodiments the contact lens comprises a single LED.

In some embodiments, the design of the electronic module will be driven by the need to keep clear the central optical zone of the contact lens in order to maintain maximum visibility, minimum interference with field of view and minimum reduction in oxygen permeability. The electronics will be preferably placed in an annular zone about 1.0-2.0 mm wide, and with an inner radius of 1.5-3.5 mm. In some embodiments, no more than 40 degrees of arc will be occupied by the microLED arrays and the electronics. The main components may comprise one or more of a microcontroller including a voltage ramp, a battery that may be a primary (non-rechargeable) battery, or a secondary (rechargeable) battery, a flash memory, a sensor, or a radiofrequency identification ("RFID") module (if used). These components may comprise part of the microcontroller or a custom made application specific integrated circuit ("ASIC"). Preferably power consumption by the microLED arrays will be in the range of 30 nanowatt to 1 microwatt, so that daily use will consume about 0.25 microwatt hour to 8 microwatt hour, operating at 3.4 volts. Therefore, a lens designed for 1 month's use will consume about 7.5 microwatt hour to about 250 microwatt hour, weighing in the range 30-50 milligrams. A solid state primary lithium battery can be used to achieve a thickness of less than 50 microns and weight in the range of 10-20 mg can be used for this application. The preferred range of open circuit voltage of these batteries (rechargeable and primary cells) is 3.0 v to 4.2 volts, since batteries operating in the range of 1.0-2.0 volts may require a voltage ramp up, that may cause loss of energy due to the up conversion, while batteries providing higher open circuit voltages will be less efficient since it is not desirable to drive the electronics beyond a voltage of 3.0 v. Most LEDs rely on about 3.0 v to 4.0 v to operate, in accordance with some embodiments.

The microLED array may be turned ON or OFF at predetermined intervals, or upon actuation by the wearer. For example, sensor such as a piezoelectric sensor or a photo sensor may be added to the MCU or ASIC module that senses blinks and provides an actuation signal that turns power ON or OFF to the LEDs. A logic built into the firmware of the microcontroller or ASIC analyzes the signal generated by the sensor and provides a command to the voltage ramp that provides power to the LEDS when a certain preprogrammed signal profile is recognized. This preprogrammed profile may be generated by the sensor such as the piezoelectric sensor when a particular blink sequence is executed by the wearer. Such an artificial blink sequence is selected by analyzing profiles of blinks that occur naturally, so that the intended blink sequence designed to trigger an ON or OFF signal is not accidentally generated. For example, the circuitry and sensor can be configured to identify a sequence of eye lid closures and eyelid openings, in which the eye is closed a plurality of times and the eye is opened a plurality of times. In some embodiments, the circuitry is configured with instructions to recognize an ON/OFF user command in response to the eye being closed longer than open a plurality of times in the sequence, which can be different than a normal blinking pattern of the eyelid.

In some embodiments, a remote unit capable of wirelessly recharging the rechargeable battery is also provided. This remote unit is preferably placed on the bedside of the wearer, and wirelessly recharges the battery in the contact lens over a distance of 20 cm to 1 meter. Alternatively, the contact lens is removed from the eye, placed in a saline or disinfecting solution for cleaning while being placed close to a remote recharging unit.

Figure 4B:
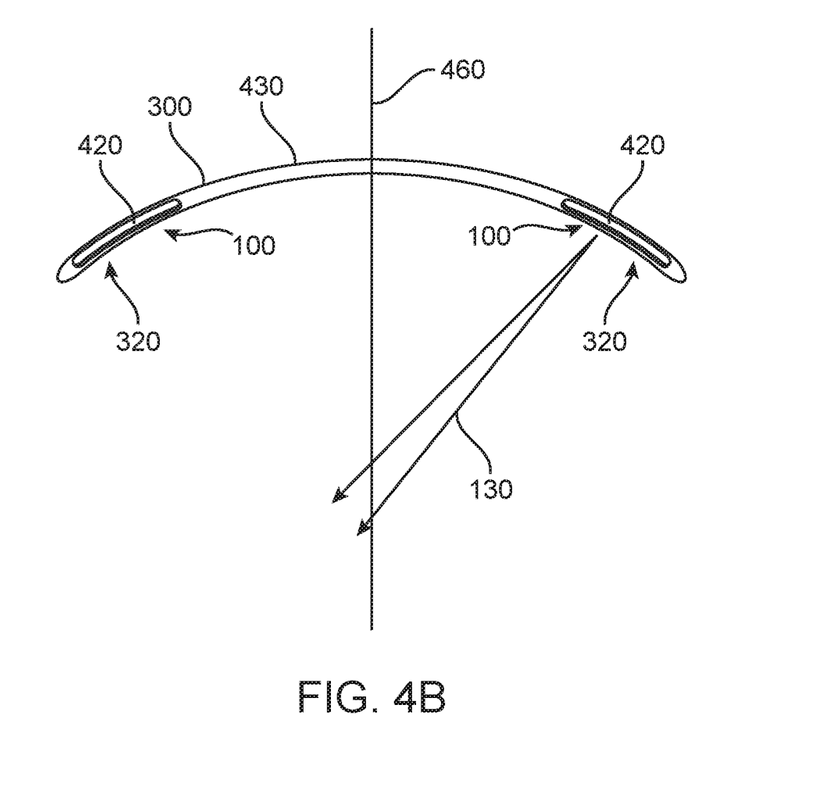
FIG. 4B shows a side cross-sectional view of a contact lens as in FIG. 4A

FIG. 4B shows a side cross-sectional view of a contact lens as in FIG. 4A. In some embodiments, light 130 from the light source such as LED array is directed toward an optical axis 460 of the contact lens. The angle of the light rays from the LED can be arranged to illuminate an area of the retina away from the fovea as described herein. In some embodiments, light from the LED is inclined in relation to the optical axis of the contact lens at angle, so as to define an angle of inclination of the light beam from the LED with respect to the optical axis of the contact lens. In some embodiments, the light 130 from the LED comprises a beam that crosses the optical axis of the contact lens to illuminate an opposite side of the retina away from the fovea as described herein, for example with a peak illumination profile away from the fovea as described herein. In some embodiments, the angle of inclination of the PCB inside the outer portion of the contact lens provides an inclination to one or more of the LEDs to illuminate the retina away from the fovea. In some embodiments, the angle of inclination of the contact lens in the outer portion away from the optical zone provides sufficient inclination so as to illuminate the retina away from the fovea.

Referring again to FIGS. 4A and 4B, the contact lens comprises an LED light source and an electronic module embedded in the contact lens. The LED light source and the electronic module configured to be worn for plurality of hours and direct light from the light source away from the fovea of the eye for the plurality of hours. The plurality of hours may comprise 8 hours, for example.

The light source can be configured to direct light away from fovea in many ways. The light source can be configured to direct light away from the fovea of the eye without forming an image on the fovea of the eye. In some embodiments, the light source is configured to direct light away from the macula of the eye. The light source can be configured to direct light to one or more of a parafoveal region, a perifoveal region, or a region outside the macula of the eye with an intensity illumination profile comprising a peak located in the one or more of the parafoveal region, the perifoveal region, or the region outside the macular of the eye. In some embodiments, the light source is configured to direct the peak to the perifoveal region or the region outside the fovea. In some embodiments, the light source is configured to direct the peak to the region outside the macula of the eye. In some embodiments, the light sources can be configured to form images on the retinal image shell. In some embodiments, this peripheral image may be formed in front of the retinal image shell, causing a myopic defocus. In some embodiments, the images can be formed behind the retinal image shell, causing a hyperopic defocus. In some embodiments, images from different light sources may be focused differently, providing an astigmatic stimulus to the retinal periphery.

The contact lens can be configured in many ways to direct light away from the fovea. In some embodiments, the LED of the LED light source is coupled to one or more of a reflector or a lens as described herein. The one or more of the reflector or the lens can be arranged to direct light away from a fovea of the eye. The LED light source and the one or more of the reflector or the lens can be arranged to direct light away from the macula with a peak intensity of illumination of the retina outside the fovea of the eye.

In some embodiments, the contact lens comprises an optical zone to correct a refractive error of the eye as described herein. For example, the LED and the one or more of the reflector or the lens can be located outside the optical zone.

The contact lens may comprise any suitable number of light sources to provide an appropriate illumination pattern on the retina to decrease dark adaptation. The light source may comprise a plurality of light sources and a plurality of one or more of reflectors or lenses located outside the optical zone arranged to direct light away from the fovea, with a peak intensity profile of each of the plurality of light sources located outside a fovea of the eye.

The optical zone may comprise a central optical axis defining an optical axis from the contact lens to the fovea, in which the peak intensity profile for each of the plurality light sources is located at an angle greater than about 5 degrees from the optical axis, for example to illuminate the retina outside the fovea. In some embodiments the angle is greater than about 8 degrees from the optical axis to illuminate the retina outside the parafovea. In some embodiments, the angle is greater than about 18 degrees from the optical axis to illuminate the eye outside the perifovea, e.g. outside the macula.

The plurality of light sources can be arranged in many ways on the contact lens. In some embodiments, the plurality of light sources is located along an annular zone outside the optical zone.

The light source can be configured in many ways. In some embodiments, the light source comprises one or more of a microLED, an organic LED (OLED), a quantum dot light emitting diode (QLED), or a cathode ray tube (CRT), for example.

The light source and one or more of the reflector or lens can be configured in many ways. In some embodiments, the light source is coupled to the one or more of the lens or the reflector as described herein to form an image of the light source in front of the retina, for example. In some embodiments, the light is coupled to one or more of the lens or a reflector configured to form an image of the light source on the retina, for example. In some embodiments, the light source is coupled to one or more of the lens or the reflector configured to form an image of the light source behind the retina.

The one or more light sources, the optical components such as reflectors or lenses, the printed circuit board, the processor and associated circuitry as described with reference to FIG. 4A, can be similarly configured with a support comprising an eyeglass frame or goggles. The eyeglass frame or googles may comprise lenses providing refractive error correction, and the electronics, light sources and lenses similarly distributed outside of the optical zone of the lenses supported with the eyeglass frame or goggles.

Contact Lens Fabrication Process

Fabrication of a contact lens with an embedded microLED has been disclosed previously and the fabrication of such lenses is known to one of ordinary skill in the art, although for other applications such as displays for augmented and virtual reality applications. The presently disclosed contact lenses can be fabricated in many ways. For example, the soft lens may be may be fabricated by cast molding or machining or 3D printing. The lens may be formed in multiple (two or more) layers or it may be formed as a single layer. In some embodiments, the microlens or microlens array with the electronics is fabricated on a circuit board and transferred to a flexible film substrate, preferably about 10-50 microns thick, but not more than 150 microns. In some embodiments, this thin film forms a two layer biocompatible package hermetically sealed at the edges encapsulating the electronic module so that the electronic components do not cause any toxic or allergic reaction to the eye. In some embodiments, the film is cut to shape and placed inside the contact lens assuming the lens is made in a multilayer process. In some embodiments, the flexible film substrate is preferably transparent, and has the same order of tensile modulus as the lens material. In some embodiments, the tensile modulus of the substrate is between 0.5 and 10× that of the contact lens material. In some embodiments, the modulus of the substrate is between 0.8 and 3.0 times the modulus of the contact lens material. In some embodiments, a soft contact lens that is provided with stabilization mechanism on the cornea provided by a slab off or double slab off optic or with thick zones on the temporal and nasal sides of the lens to prevent it from rotating when the wearer blinks. Lens stabilization can be helpful so that the microLED arrays stay in the appropriate orientation for optical coupling with the pupil.

In some embodiments, of the contact lens comprises a spherical or a toric lens, matching the refractive requirements of the wearer. This can be helpful, since many wearers may want to get up sometime during the night and go the bathroom, navigating in dim light or dark.

As detailed above, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. For example, one or more of the devices recited herein may receive image data of a sample to be transformed, transform the image data, output a result of the transformation to determine a process, use the result of the transformation to perform the process, and store the result of the transformation to produce an output image of the sample. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

A processor as described herein can be configured to perform one or more steps of any method disclosed herein.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word 37 comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination. The term "and/or" is used similarly.

As used herein, characters such as numerals refer to like elements.

The present disclosure includes the following numbered clauses. Each of these clauses can be combined with one or more other clauses in accordance with the present disclosure.

Clause 1. A contact lens comprising, a light source and an electronic module embedded in the contact lens, the light source and the electronic module configured to be worn for plurality of hours and direct light from the light source away from a fovea of an eye for the plurality of hours.

Clause 2. The contact lens of clause 1, wherein said light source is configured to direct light away from a macula of the eye.

Clause 3. The contact lens of clause 1, wherein said light source is configured to direct light away from the fovea of the eye without forming an image on the fovea of the eye.

Clause 4. The contact lens of clause 1, wherein said light source is configured to direct light to one or more of a parafoveal region, a perifoveal region, or a region outside the macula of the eye with an intensity illumination profile comprising a peak located in the one or more of the parafoveal region, the perifoveal region, or the region outside the macular of the eye, and optionally wherein said light source is configured to direct the peak to the perifoveal region or the region outside the fovea and optionally wherein said light source is configured to direct the peak to the region outside the macula of the eye.

Clause 5. The contact lens of clause 1, wherein an LED of said light source is coupled to one or more of a reflector or a lens, wherein said light source and the one or more of the reflector or the lens is arranged to direct light away from a fovea of the eye.

Clause 6. The contact lens of clause 5, wherein said LED light source and the one or more of the reflector or the lens is arranged to direct light away from the macula with a peak intensity of illumination of the retina outside the fovea of the eye.

Clause 7. The contact lens of clause 6, wherein the contact lens comprises an optical zone to correct a refractive error of the eye.

Clause 8. The contact lens of clause 7, wherein the LED and the one or more of the reflector or the lens is located outside the optical zone.

Clause 9. The contact lens of clause 8, wherein the light source comprises a plurality of light sources and a plurality of one or more of reflectors or lenses located outside the optical zone arranged to direct light away from the fovea with a peak intensity profile of each of the plurality of light sources located outside a fovea of the eye.

Clause 10. The contact lens of clause 9, wherein the optical zone comprises a central optical axis defining an optical axis from the contact lens to the fovea, and wherein the peak intensity profile for each of the plurality light sources is located at an angle greater than about 5 degrees from the optical axis and optionally greater than about 8 degrees from the optical axis and optionally greater than about 18 degrees from the optical axis.

Clause 11. The contact lens of clause 9, wherein the plurality of light sources is located along an annular zone outside the optical zone.

Clause 12. The contact lens of any one of clause 1 or clause 10, wherein the plurality of hours comprises 8 hours.

Clause 13. The contact lens of clause 1 wherein said light source comprises a plurality of LEDs and optionally wherein said plurality of LEDs comprises an array of LEDs.

Clause 14. The contact lens of clause 13 wherein a plurality of microLED arrays is disposed outside of an optical zone of said contact lens, said optical zone shaped to correct a refractive error of the wearer.

Clause 15. The contact lens of clause 1, wherein said electronic module is hermetically sealed in a biocompatible package of a thickness not exceeding 150 microns.

Clause 16. The contact lens of clause 1, wherein said light source emits radiation with a peak within a range from about 490 to about 510 nanometers.

Clause 17. The contact lens of clause 1, wherein said LED light source emits radiation with a bandwidth not exceeding 25 nanometers.

Clause 18. The contact lens of clause 1, wherein a power of said LED light source is in a range of 0.05 to 0.5 candelas over a pupillary aperture of the eye in a range of 2.5 mm to 6.0 mm.

Clause 19. The contact lens of clause 1, wherein said light source is optically coupled to a lens to direct light away from a fovea of the eye.

Clause 20. The contact lens of clause 1, wherein said electronic module comprises one or more of a processor, a sensor to detect an eyelid, a battery to provide electric power, a memory, or an RFID module and wherein said sensor comprises one or more of a piezo electric sensor or a photo sensor detect an eyelid on the lens.

Clause 21. The contact lens of clause 1 or clause 20, wherein said electronic module comprises a printed circuit board having an arcuate shape, said printed circuit board disposed on an outer portion of the contact lens no less than 1.5 mm from a center of said contact lens.

Clause 22. The contact lens of clause 1 or clause 20, wherein said light source is triggered ON or OFF by an actuation signal from a sensor.

Clause 23. The contact lens of clause 1 or clause 20, wherein said electronic module is coupled to said light and a sensor, said electronic module configured with instructions to turn said light source ON or OFF in response to a blink sequence received from said sensor.

Clause 24. The contact lens of clause 1 or clause 20, wherein a battery comprises a rechargeable battery with an open circuit voltage range of 3.0 v to 4.0 v.

Clause 25. The contact lens of clause 1 or clause 20, wherein a battery comprises a solid state battery.

Clause 26. The contact lens of clause 1 or clause 1 wherein said RFID module wirelessly recharges said battery.

Clause 27. The contact lens of clause 1, wherein said contact lens is designed to decrease dark adaptation in a wearer when the wearers is in the dark or asleep.

Clause 28. The contact lens of clause 1, wherein said contact lens is designed to slow down progressive retinal damage due to diabetic retinopathy.

Clause 29. The contact lens of clause 1, wherein said light source comprises one or more of a microLED, an organic LED (OLED), a quantum dot light emitting diode (QLED), or a cathode ray tube (CRT).

Clause 30. The contact lens of clause 1, wherein said light is coupled to one or more of a lens or a reflector configured to form an image of the light source in front of the retina.

Clause 31. The contact lens of clause 1, wherein said light is coupled to one or more of a lens or a reflector configured to form an image of the light source on the retina.

Clause 32. The contact lens of clause 1, wherein said light is coupled to one or more of a lens or a reflector configured to form an image of the light source behind the retina.

Clause 33. A contact lens comprising, a microLED light source and an electronic module embedded in the contact lens, the microLED light source and the electronic module configured to be worn for several hours at a time.

Clause 34. The contact lens of clause 33 wherein said microLED light source comprises an array of microLEDs.

Clause 35. The contact lens of clause 34 wherein a plurality of microLED arrays is disposed on or about a peripheral optical zone of said contact lens.

Clause 36. The contact lens of clause 33, wherein said electronic module is hermetically sealed in a biocompatible package of a thickness not exceeding 150 microns.

Clause 37. The contact lens of clause 33, wherein said light source emits radiation at 500 nanometers.

Clause 38. The contact lens of clause 33, wherein said microLED light source emits radiation with a bandwidth not exceeding 25 nanometers.

Clause 39. The contact lens of clause 33, wherein a power of said microLED light source is in a range of 0.05 to 0.5 candelas over a pupillary aperture in a range of 2.5 mm to 6.0 mm.

Clause 40. The contact lens of clause 33, wherein said microLED light source is interfaced with a microlens array.

Clause 41. The contact lens of clause 33, wherein said electronic module comprises a microcontroller or ASIC, a piezoelectric sensor, a battery to provide electric power, a flash or nonvolatile memory and an RFID module.

Clause 42. The contact lens of clause 33 or clause 41, wherein said electronic module is built in an arcuate shape disposed on a periphery of the contact lens no less than 1.5 mm from a center of said contact lens.

Clause 43. The contact lens of clause 33 or clause 41, wherein said microLED light source is triggered ON or OFF by an actuation signal from a sensor.

Clause 44. The contact lens of clause 33 or clause 41, wherein said microLED light source is turned ON or OFF by a specific blink sequence that does not occur naturally.

Clause 45. The contact lens of clause 33 or clause 41, wherein a battery is a rechargeable battery with an open circuit voltage range of 3.0 v to 4.0 v.

Clause 46. The contact lens of clause 33 or clause 41, wherein a battery is a solid state battery.

Clause 47. The contact lens of clause 41 or clause 46 wherein said RFID module wirelessly recharges said battery.

Clause 48. The contact lens of clause 33, wherein said contact lens is designed to inhibit dark adaptation in a wearer when the wearer is in the dark or asleep.

Clause 49. The contact lens of clause 33, wherein said contact lens is designed to slow down progressive retinal damage due to diabetic retinopathy.

Clause 50. The contact lens of any one of the preceding clauses, wherein said contact lens is configured to inhibit dark adaptation with an amount of light to a wearer's eye when in the dark or asleep and wherein the amount of light comprises no more than 25 Candela (cd) per square meter ($m^2$).

Clause 51. The contact lens of any one of the preceding clauses, further comprising a contact lens body, said contact lens body comprising a hydrogel, and wherein said microLED light source and said electronic module are embedded in the contact lens body.

Clause 52. A device to decrease dark adaptation of an eye of a wearer, the device comprising:
 a light source comprising one or more LEDs;
 a support to couple light from the one or more LEDs to the eye of the wearer and direct to light to a location away from a fovea of the wearer, the support comprising one or more of a contact lens, an eyeglasses frame, or goggles.

Clause 53. The device of clause 52, further comprising one or more of lenses or reflectors coupled to the one or more LEDs to direct light from the light source to the location away from the fovea.

Embodiments of the present disclosure have been shown and described as set forth herein and are provided by way of example only. One of ordinary skill in the art will recognize numerous adaptations, changes, variations and substitutions without departing from the scope of the present disclosure. For example, although reference is made to contact lenses configured to decrease dark adaptation to treat retinal disease, the configurations and arrangements of the contact lenses disclosed herein can similarly be practiced with eyeglasses and goggles. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

The invention claimed is:

1. A contact lens to decrease a hypoxia of a retina of an eye of a wearer, the contact lens comprising, a light source coupled to one or more of a lens or a reflector and an electronic module embedded in the contact lens, the light source and the electronic module configured to be worn for a plurality of hours and direct light from the light source away from a fovea of the eye of the wearer for the plurality of hours, the one or more of the lens or the reflector configured to form an image of the light source behind or in front of the retina;
   wherein the contact lens comprises an optical zone to correct a refractive error of the eye;
   wherein the light source comprises a plurality of light sources and a plurality of one or more of reflectors or lenses located outside the optical zone and arranged to direct light away from the fovea with a peak intensity profile of each of the plurality of light sources located outside the fovea of the eye to decrease the hypoxia when the wearer sleeps, and wherein all light sources of the contact lens are arranged to direct light away from the fovea.

2. The contact lens of claim 1, wherein said light source is configured to direct light away from a macula of the eye.

3. The contact lens of claim 1, wherein said light source is configured to direct light away from the fovea of the eye without forming an image on the fovea of the eye.

4. The contact lens of claim 1, wherein said light source is configured to direct light to one or more of a parafoveal region, a perifoveal region, or a region outside a macula of the eye with an intensity illumination profile comprising a peak located in the one or more of the parafoveal region, the perifoveal region, or the region outside the macula of the eye.

5. The contact lens of claim 1, wherein the light source comprises an LED that is coupled to the one or more of the lens or the reflector.

6. The contact lens of claim 5, wherein said LED light source and the one or more of the reflector or the lens is arranged to direct light away from a macula with a peak intensity of illumination of the retina outside the macula of the eye.

7. The contact lens of claim 1, wherein the optical zone comprises a central optical axis defining an optical axis from the contact lens to the fovea, and wherein the peak intensity profile for each of the plurality of light sources is located at an angle greater than about 5 degrees from the optical axis.

8. The contact lens of claim 1, wherein the plurality of light sources is located along an annular zone outside the optical zone.

9. The contact lens of claim 1, wherein the plurality of hours comprises 8 hours.

10. The contact lens of claim 1 wherein said light source comprises a plurality of LEDs.

11. The contact lens of claim 10 wherein the contact lens comprises the optical zone and the plurality of LEDs is disposed outside of the optical zone of said contact lens, said optical zone shaped to correct the refractive error of the wearer.

12. The contact lens of claim 1, wherein said electronic module is hermetically sealed in a biocompatible package of a thickness not exceeding 150 microns.

13. The contact lens of claim 1, wherein said light source emits radiation with a peak within a range from about 490 to about 510 nanometers.

14. The contact lens of claim 1, wherein said light source emits radiation with a bandwidth not exceeding 25 nanometers.

15. The contact lens of claim 1, wherein a power of said light source is in a range of 0.05 to 0.5 candelas over a pupillary aperture of the eye in a range of 2.5 mm to 6.0 mm.

16. The contact lens of claim 1, wherein said electronic module comprises a printed circuit board having an arcuate shape, said printed circuit board disposed on an outer portion of the contact lens no less than 1.5 mm from a center of said contact lens.

17. The contact lens of claim 1, further comprising a sensor, wherein said light source is triggered ON or OFF by an actuation signal from the sensor.

18. The contact lens of claim 1, further comprising a sensor, wherein said electronic module is coupled to said light source and the sensor, said electronic module configured with instructions to turn said light source ON or OFF in response to a blink sequence received from said sensor.

19. The contact lens of claim 1, further comprising an RFID module and a battery, wherein the RFID module wirelessly recharges the battery.

20. The contact lens of claim 1, wherein said light source comprises one or more of a microLED, an organic LED (OLED), a quantum dot light emitting diode (QLED), or a cathode ray tube (CRT).

* * * * *